United States Patent
Shinada et al.

(10) Patent No.: US 9,791,410 B2
(45) Date of Patent: Oct. 17, 2017

(54) DISCHARGE IONIZATION CURRENT DETECTOR

(75) Inventors: Kei Shinada, Uji (JP); Shigeyoshi Horiike, Uji (JP); Takahiro Nishimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 323 days.

(21) Appl. No.: 14/123,582

(22) PCT Filed: May 31, 2012

(86) PCT No.: PCT/JP2012/064045
§ 371 (c)(1),
(2), (4) Date: Dec. 23, 2013

(87) PCT Pub. No.: WO2012/169419
PCT Pub. Date: Dec. 13, 2012

(65) Prior Publication Data
US 2014/0145724 A1 May 29, 2014

(30) Foreign Application Priority Data
Jun. 7, 2011 (JP) ................. 2011-126895

(51) Int. Cl.
*G01N 27/62* (2006.01)
*G01N 30/64* (2006.01)
(Continued)

(52) U.S. Cl.
CPC .......... *G01N 27/62* (2013.01); *G01N 27/70* (2013.01); *G01N 30/64* (2013.01); *G01R 19/0061* (2013.01)

(58) Field of Classification Search
CPC ........ G01N 27/62; G01N 27/64; G01N 27/68; G01N 27/70; G01N 30/64; G01R 19/0061;
(Continued)

(56) References Cited

U.S. PATENT DOCUMENTS 4,266,196 A * 5/1981 Kawazoe ............... G01N 27/66
313/231.71
5,394,092 A * 2/1995 Wentworth ............ G01N 27/70
324/455
(Continued)

FOREIGN PATENT DOCUMENTS

CN 101207966 A 6/2008
CN 101953235 A 1/2011
(Continued)

OTHER PUBLICATIONS

Nishimoto et al., "Evaluation of Silanol Concentration on Quartz Glass Surface for EOF Stability of CE Chip", Micro Total Analysis Systems, 595-596, (2001).
(Continued)

*Primary Examiner* — Hoai-An D Nguyen
(74) *Attorney, Agent, or Firm* — Morgan, Lewis & Bockius LLP

(57) ABSTRACT

A low-OH-content quartz glass with an OH content equal to or lower than 5 ppm is used as a cylindrical tube (2) covering the surface of metallic plasma generation electrodes (4, 5 and 6) for generating a low-frequency barrier discharge. It has been found that, in the low-frequency barrier discharge, hydrogen and oxygen originating from the OH contained in a dielectric material are released into plasma gas for a long period of time, constituting a primary cause of an increase in the baseline current. The use of a low-OH-content quartz glass dramatically lowers the baseline current and thereby improves the S/N ratio and the detection limit.

6 Claims, 3 Drawing Sheets

(51) Int. Cl.
  *G01N 27/70* (2006.01)
  *G01R 19/00* (2006.01)
(58) Field of Classification Search
  CPC ........ H01J 47/00; H01J 47/02; H01J 47/1211;
      H01J 47/1233; H01J 47/125; H01J
      47/1255; H01J 47/1283; H01J 49/00;
      H01J 49/02; H01J 49/06; H01J 49/08;
      H01J 49/10; H01J 49/107; H01J 49/14;
      H01J 40/00
  USPC ........ 324/459, 464; 250/281, 282, 283, 285,
      250/299, 300
  See application file for complete search history.

(56) References Cited

U.S. PATENT DOCUMENTS

| | | | | |
|---|---|---|---|---|
| 5,889,404 A * | 3/1999 | Abdel-Rahman | ...... | G01N 27/70 250/423 R |
| 6,333,632 B1 * | 12/2001 | Yang | ...... | G01N 27/70 324/459 |
| 7,768,267 B2 * | 8/2010 | Knott | ...... | G01L 21/34 250/397 |
| 8,736,287 B2 * | 5/2014 | Dhirani | ...... | G01N 27/4473 204/403.01 |
| 9,188,570 B2 * | 11/2015 | Stearns | ...... | G01N 30/64 |
| 2009/0031785 A1 * | 2/2009 | Kellner | ...... | G01N 27/68 73/23.39 |
| 2009/0196765 A1 | 8/2009 | Dyer et al. | | |
| 2011/0018546 A1 * | 1/2011 | Kitano | ...... | G01N 27/68 324/464 |
| 2011/0133746 A1 * | 6/2011 | Shinada | ...... | G01N 30/64 324/464 |
| 2011/0187379 A1 * | 8/2011 | Shinada | ...... | G01N 27/70 324/464 |

FOREIGN PATENT DOCUMENTS

| | | |
|---|---|---|
| CN | 101981441 A | 2/2011 |
| EP | 2245911 A1 | 11/2010 |
| JP | 2009-302134 A | 12/2009 |
| JP | 2010-60354 | 3/2010 |
| JP | 2011-511615 A | 4/2011 |
| WO | 2009/097068 A1 | 8/2009 |
| WO | 2009/119050 A1 | 10/2009 |

OTHER PUBLICATIONS

International Search Report dated Jul. 10, 2012 for International Application No. PCT/JP2012/064045 (2pgs).
Examination Report Received for Chinese Patent Application No. 201280011760.1 dated Oct. 28, 2014, 8 pages (2 pages of English Translation & 6 pages of Official copy).
First Office Action issued in a corresponding Japanese Patent Application No. 2014-100427, dated May 26, 2015.

* cited by examiner

DISCHARGE IONIZATION CURRENT DETECTOR

RELATED APPLICATIONS

This application is the U.S. national stage application of International (PCT) Patent Application Serial No. PCT/JP2012/064045, filed May 31, 2012, which claims the benefit of JP Application No. 2011-126895, filed Jun. 7, 2011. The entire disclosure of each of these applications is hereby incorporated by reference.

TECHNICAL FIELD

The present invention relates to a discharge ionization current detector primarily suitable as a detector for a gas chromatograph (GC), and more specifically, to a discharge ionization current detector using a low-frequency barrier discharge.

BACKGROUND ART

As a detector for a gas chromatograph, various types of detectors have been practically applied, such as a thermal conductivity detector (TCD), electron capture detector (ECD), flame ionization detector (FID), flame photometric detector (FPD), and flame thermionic detector (FTD). Among these detectors, the FID is most widely used, particularly for the purpose of detecting organic substances. The FID is a device that ionizes sample components in a sample gas by hydrogen flame and detects the resultant ion current. It can attain a wide dynamic range of approximately six orders of magnitude. However, the FID has the following drawbacks: (1) Its ionization efficiency is low, so that its minimum detectable amount is not adequately low; (2) Its ionization efficiencies for alcohols, aromatic substances, and chlorine substances are low; (3) It requires hydrogen, which is a highly hazardous substance; therefore, an explosion-proof apparatus or similar kind of special equipment must be provided, which makes the entire system difficult to operate.

On the other hand, a pulsed discharge detector (PDD) has conventionally been known as a detector capable of high-sensitivity detection of a wide variety of compounds ranging from inorganic substances to low-boiling-point organic compounds (see Patent Document 1 or other documents). In the PDD, the molecules of helium or another substance are excited by a high-voltage pulsed discharge. When those molecules return from their excited state to the ground state, they generate light energy. This light energy is utilized to ionize a molecule to be analyzed, and an ion current produced by the generated ions is detected to obtain a detection signal corresponding to the amount (concentration) of the molecule to be analyzed.

In most cases, the PDD can attain higher ionization efficiencies than the FID. For example, the ionization efficiency of the FID for propane is no higher than 0.0005%, whereas the PDD can achieve a high level of approximately 0.07%. However, the dynamic range of the PDD is not as wide as that of the FID; the fact is that the former is lower than the latter by one or more orders of magnitude. This is one of the reasons why the PDD is not as widely used as the FID.

The most probable constraining factors for the dynamic range of the conventional PDD are the unstableness of the plasma created for the ionization and the periodic fluctuation of the plasma state. To solve this problem, a discharge ionization current detector has been proposed (for example, see Patent Documents 2 and 3), which uses a low-frequency AC-excited dielectric barrier discharge (which is hereinafter referred to as the "low-frequency barrier discharge") to create a stable and steady state of plasma. The low-frequency barrier discharge is featured by the use of an electrode covered with a dielectric member for generating an electric discharge; such an electrode releases a smaller amount of thermions, secondary electrons and similar particles than metallic electrodes, and therefore, can produce plasma with high stability. The excitation of helium or other elements by a low-frequency high voltage leads to the creation of non-equilibrium plasma at a very low gas temperature (with almost no generation of heat), which suppresses the generation of the gas of impurities due to the heating of the materials in the inner wall of the gas tube, so that the plasma stability is even further improved. The stabilization of the plasma has the effect of stabilizing the ionization efficiency and thereby reduces the noise in the ionization current output. Thus, the ionization current detector using a low-frequency barrier discharge can achieve a high signal-to-noise ratio (S/N).

BACKGROUND ART DOCUMENT

Patent Document

Patent Document 1: U.S. Pat. No. 5,394,092B2
Patent Document 2: WO 2009/119050
Patent Document 3: JP-A 2010-60354

SUMMARY OF THE INVENTION

Problem to be Solved by the Invention

However, the ionization current detector using the low-frequency barrier discharge has the following problem:

In general, in a discharge ionization current detector, a steady-state current called the baseline current or background current (these types of electric current are hereinafter called the "baseline current") is detected even when no sample gas is being supplied, i.e. when only the carrier gas and plasma gas are passing through the detector. There are various possible causes for the baseline current, but the primary cause is the current due to the ionization of an impurity contained in the carrier gas and the plasma gas. The baseline current is a steady-state current and does not affect chromatogram peaks. However, when the baseline current is high, i.e. when the gas contains a large amount of impurity, the following problems may possibly occur: (1) if the baseline current fluctuates under the influence of a change in the temperature or other conditions of the surrounding environment, the fluctuation will be observed as a noise and the S/N ratio deteriorates; and (2) if the source of the released impurity is the inner wall of the gas tube or similar elements, the impurity will cause a long-term drift. Accordingly, it is preferable to use high-purity carrier gas or plasma gas and supply the gas through a clean tube so as to make the baseline current as low as possible. Taking such measures requires a considerable amount of cost and yet does not absolutely ensure that the baseline current will be adequately suppressed.

The present invention has been developed in view of the previously described problem. Its objective is to provide a discharge ionization current detector in which the accuracy and sensitivity of the measurement can be improved by suppressing the baseline current to a level lower than that of the conventional systems.

Means for Solving the Problem

When an emission spectrum of plasma generated by a low-frequency barrier discharge in a conventional system is observed, emissions other than that of the excited species, i.e. helium, are also found, such as the emission of H (hydrogen atoms) at approximately 656 nm and that of O (oxygen atoms) at 777 nm. In general, it is the light of the ultraviolet region that contributes to the ionization of sample components in a discharge ionization current detector. Therefore, it has been believed that the aforementioned emissions of light within a wavelength range from red through near-infrared regions barely affect the ionization. However, various experiments conducted by the present inventors have revealed that the very presence of H and O has some influence on an increase in the baseline current, and that the dielectric member which covers the electrode and is exposed to the plasma is the supply source of H and O. Since dielectric materials, such as quartz glass, generally contain the hydroxyl group (OH), it is predictable that a certain amount of H and O will be released in the initial phase of use. In the case of the discharge ionization current detector using a low-frequency barrier discharge, it can be inferred that, since the dielectric member is directly and continuously exposed to the plasma, not only the OH groups in the vicinity of the surface of the dielectric layer but also those which initially exist in slightly deeper regions move to the surface, causing a continuous release of H and O for a comparatively long period of time.

The discharge ionization current detector according to a first aspect of the present invention has been developed on the basis of the previously described finding, which includes: a discharge electrode having a surface covered with a dielectric member and provided so as to be exposed to the inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by the action of the plasma in the gas passage, wherein quartz glass with a hydroxyl-group content equal to or lower than 5 ppm is used as the dielectric member.

Quartz glass used as a material for a jig in a semiconductor producing process or for various kinds of optical devices is roughly divided into categories of fused quartz glass and synthetic quartz glass. In any case, quartz glass with a hydroxyl-group content equal to or lower than 5 ppm is used for high-accuracy infrared optical members or similar components which may cause problems due to the absorption of light by the hydroxyl group.

A second aspect of the present invention is characterized in that a material prepared by performing a heat treatment on quartz glass with an upper limit of the hydroxyl-group content higher than 5 ppm at a temperature of 500° C. or higher in a predetermined kind of inert-gas atmosphere is used in place of the dielectric member in the discharge ionization current detector according to the first aspect of the present invention.

If a high-purity quartz glass with a carboxyl-group content of approximately 200 ppm is subjected to a heat treatment at a temperature of 1000° C. or higher for eight hours in $N_2$ atmosphere, the hydroxyl-group content will be decreased to 5 ppm or lower within a depth range from the surface of the glass to a depth of approximately 2 μm. The requirement of the heat treatment in the second aspect of the present invention is to control the heat-treatment conditions (temperature and time) so that the hydroxyl-group content will be equal to or lower than 5 ppm within the aforementioned depth range.

Sapphire or high-purity alumina may also be used in place of the quartz glass with a low hydroxyl-group content used as the dielectric member in the discharge ionization current detector according to the first aspect of the present invention.

A dielectric member having a thin-film layer made of a dielectric material with a hydroxyl-group content equal to or lower than 5 ppm and forming a 2-μm depth range from the surface coming in contact with plasma may also be used in place of the quartz glass with a low hydroxyl-group content used as the dielectric member in the discharge ionization current detector according to the first aspect of the present invention.

The plasma gas used in the discharge ionization current detector according to the present invention may be any gas selected from the group of helium, argon, nitrogen, neon and xenon, or any mixture of two or more of them. If the sample gas needs to be diluted, the same gas as the plasma gas can also be used as the dilution gas. The frequency of the low-frequency alternating voltage can be set within a range from 1 kHz to 100 kHz.

Effect of the Invention

In the discharge ionization current detector according to the present invention, either a dielectric material which itself has a low hydroxyl-group content, or a dielectric material that has undergone a heat treatment by which the hydroxyl-group content is lowered at least within a predetermined depth range from the surface to be in contact with plasma, is used as the dielectric member covering the electrode body made of a metal or similar conductor. By this design, the concentration of the impurities mainly composed of hydrogen and oxygen released from the discharge electrode into the plasma gas is made to be lower than in the case where a normal kind of quartz glass or similar dielectric material is used. In particular, even if the dielectric member covering the surface of the discharge electrode is continuously exposed to plasma during a long-term operation, the concentration of the impurities released into the plasma gas is maintained at low levels. Therefore, the baseline current is suppressed, and the fluctuation in the baseline current due to a change in the surrounding environment or the like is also suppressed. As a result, the noise is reduced and the S/N ratio is improved. The detection limit will also be improved; it is possible to achieve a detection limit comparable to or even better than the levels achieved by FIDs currently and widely used as detectors for GCs. Furthermore, with the discharge ionization current detector according to the present invention, the long-term drift of the detection signal will also be decreased, since the original amount of impurities released into the gas tube is small and its fluctuation is also small.

BRIEF DESCRIPTION OF THE DRAWINGS

FIG. 2A is a graph with a linear scale and FIG. 2B is a graph with a logarithmic scale.

BEST MODE FOR CARRYING OUT THE INVENTION

Figure 1:
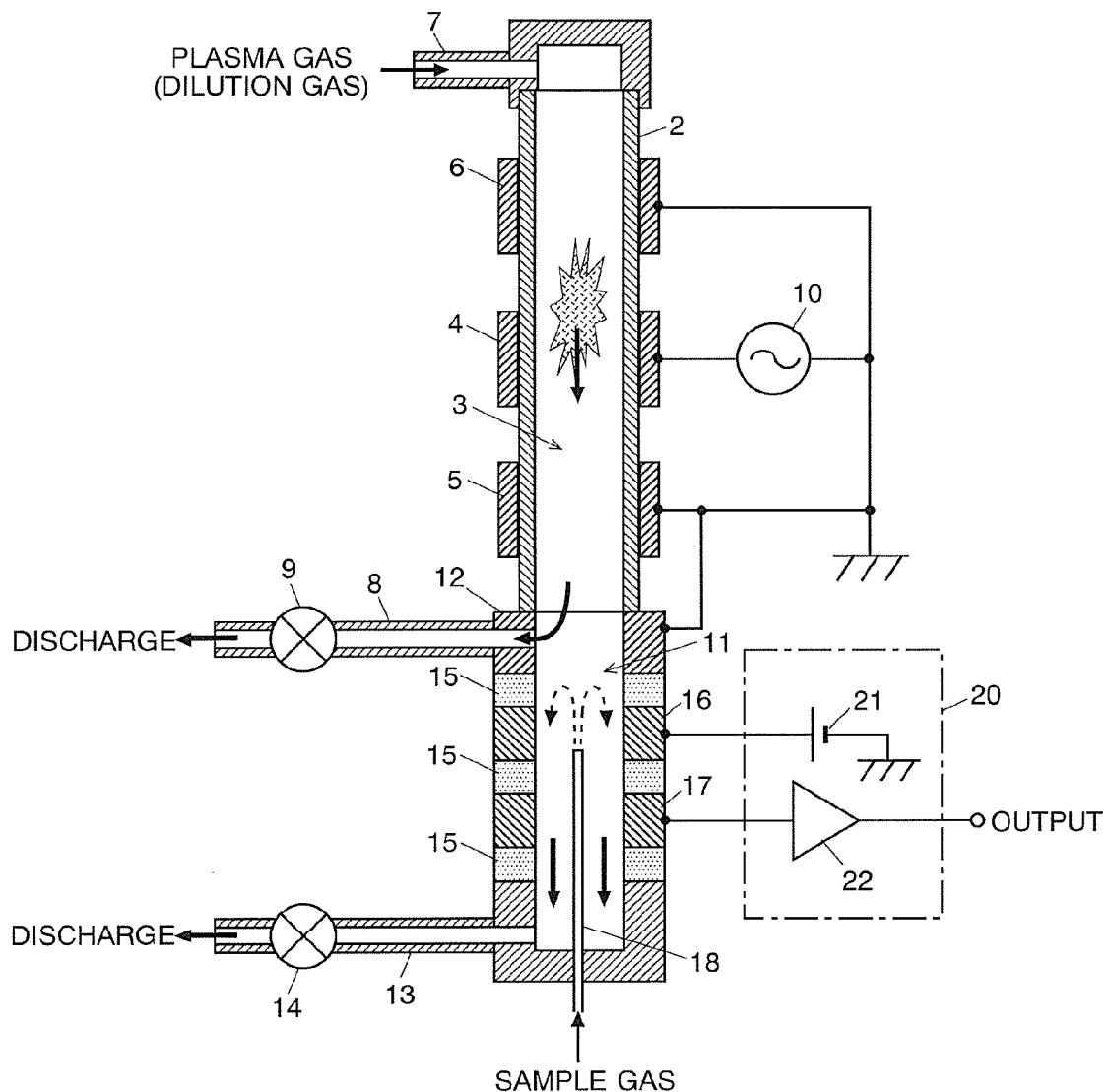
FIG. 1 is a schematic configuration diagram of a discharge ionization current detector according to one embodiment of the present invention.

A discharge ionization current detector according to one embodiment of the present invention is hereinafter described with reference to FIG. 1. FIG. 1 is a schematic configuration diagram of the discharge ionization current detector according to the present embodiment.

In the discharge ionization current detector of the present embodiment, the inner space of a cylindrical tube 2 made of a dielectric material serves as a first gas passage 3. Ring-shaped plasma generation electrodes 4, 5 and 6 made of a metal (e.g. stainless steel or copper) are circumferentially provided at predetermined intervals on the outer wall surface of the cylindrical tube 2. The presence of the wall of the cylindrical tube 2 between the first gas passage 3 and each of the plasma generation electrodes 4, 5 and 6 means that this wall, which is made of a dielectric material, can function as a dielectric coating layer which covers the electrodes 4, 5 and 6, thus enabling a dielectric barrier discharge to occur. A gas supply tube 7 is connected to the upper end of the cylindrical tube 2. A plasma gas, which doubles as a dilution gas, is supplied through this gas supply tube 7 into the first gas passage 3.

Among the three plasma generation electrodes 4, 5 and 6, the central plasma generation electrode 4 is connected to an excitation high-voltage power source 10, while the plasma generation electrodes 5 and 6 located on both sides of that plasma generation electrode 4 are connected to a ground. The structure in which the plasma generation electrode 4, to which the high voltage is applied, is sandwiched between the grounded plasma generation electrodes 5 and 6 prevents the plasma produced by the electric discharge from spreading toward the upstream (downward in FIG. 1) and downstream (upward in FIG. 1) ends of the gas stream, thus limiting the substantial plasma generation area to the space between the two plasma generation electrodes 5 and 6. The excitation high-voltage power source 10 generates a low-frequency high AC voltage. Its frequency is within a range from 1 kHz to 100 kHz, and more preferably from 5 kHz to 50 kHz. The AC voltage may have any waveform, such as sine waves, rectangular waves, triangular waves or sawtooth waves.

In the lower portion of the cylindrical tube 2, a recoil electrode 12, a bias electrode 16 and an ion-collecting electrode 17 are arranged, with insulating members 15 made of alumina, PTFE resin or a similar material provided between them. Each of these electrodes consists of a cylindrical body having the same inner diameter. These cylindrical bodies internally form a second gas passage 11 continuously extending from the first gas passage 3 in the cylindrical tube 2. Therefore, the recoil electrodes 12, the bias electrodes 16 and the ion-collecting electrode 17 are directly exposed to the gas inside the second gas passage 11. The recoil electrode 12, which is located at the connecting portion of the first gas passage 3 and the second gas passage 11, is connected to a ground and prevents the charged particles in the plasma from reaching the ion-collecting electrode 17, whereby the noise is reduced and the S/N ratio is improved. The bias electrode 16 is connected to a bias DC power source 21 included in an ion-current detector 20, while the ion-collecting electrode 17 is connected to a current amplifier 22 which is also included in the ion current detector 20. In the second gas passage 11, the space inside the bias electrode 16, the ion-collecting electrode 17 and the intervening section corresponds to the substantial current detection area.

A first gas discharge tube 8 is connected to the upper end of the cylindrical tube 2, i.e. to the end of the first gas passage 3 which corresponds to the terminal end if the connection point of the gas supply tube 7 is regarded as the beginning end of the first gas passage 3. The first gas discharge tube 8 has a first flow-rate regulator 9. On the other hand, a second gas discharge tube 13 is connected to the end of the second gas passage 11 which corresponds to the terminal end if the connection point of the first gas discharge tube 8 is regarded as the beginning end of the gas passage 11. The second gas discharge tube 13 has a second flow-rate regulator 14. A sample introduction tube 18 with a small diameter is inserted in the second gas passage 11, through which a sample gas containing a sample component to be analyzed is supplied to a position near the connection point of the first gas discharge tube 8 in the second gas passage 11.

A detecting operation of this discharge ionization current detector is hereinafter described.

As shown by the arrow in FIG. 1, a plasma gas is supplied through the gas supply tube 7 into the first gas passage 3. The plasma gas is a kind of gas that can be easily ionized. For example, any gas selected from the group of helium, argon, nitrogen and neon, or any mixture of two or more of them, can be used as the plasma gas. The flow rates of the first and second flow-rate regulators 9 and 14 are individually preset at appropriate values. With L1 denoting the flow rate of the gas through the first gas discharge tube 8 adjusted with the first flow-rate regulator 9 and L2 denoting the flow rate of the gas through the second gas discharge tube 13 adjusted with the second flow-rate regulator 14, the flow rate of the gas supplied through the gas supply tube 7 is L1+L2.

As shown in FIG. 1, the plasma gas flows downwards through the first gas passage 3 and passes through the plasma generation area, with a portion of the gas (at flow rate L1) being discharged through the first gas discharge tube 8 to the outside. The remaining portion of the gas (at flow rate L2), which serves as the dilution gas, flows downwards through the second gas passage 11. After being mixed with a sample gas supplied through the sample introduction tube 18, the plasma gas passes through the current detection area, to be eventually discharged through the second gas discharge tube 13 to the outside.

While the plasma gas is flowing through the first gas passage 3 in the previously described manner, the excitation high-voltage power source 10 is energized, whereupon the excitation high-voltage power source 10 applies a low-frequency high AC voltage between the plasma generation electrode 4 and each of the other plasma generation electrodes 5 and 6. As a result, an electric discharge occurs in the plasma generation area between the plasma generation electrodes 5 and 6 in the first gas passage 3. This discharge is a dielectric barrier discharge since it occurs through the dielectric coating layer (i.e. the cylindrical tube 2). Due to this dielectric barrier discharge, the plasma gas flowing through the first gas passage 3 is ionized over a wide range, producing a cloud of plasma (i.e. atmospheric non-equilibrium micro-plasma).

The excitation light emitted from the atmospheric non-equilibrium micro-plasma passes through the first gas passage 3 and then the second gas passage 11 to the area where the sample gas exists, and ionizes the molecules (or atoms) of the sample component in the sample gas. Due to the effect of the bias DC voltage applied to the bias electrode 16, the generated sample ions give electrons to or receive electrons from the ion-collecting electrode 17. As a result, an ion current corresponding to the amount of the generated sample ions, i.e. the amount of the sample component, is sent to the current amplifier 22, which amplifies the current and outputs it as the detection signal. In this manner, the present discharge ionization current detector produces a detection signal corresponding to the amount (concentration) of the sample component contained in the introduced sample gas.

The flow rate L2 of the dilution gas flowing through the second gas passage 11 can be previously set so as to achieve an appropriate dilution ratio for the sample concentration range to be measured. In particular, if the sample concentration is low, the gas flow rate L2 should be lowered, whereby the sample gas is allowed to pass through the current detection area without being much diluted, so that a trace component can be detected with high sensitivity. Thus, a high-sensitivity detection can be performed while ensuring the stability of the plasma and achieving a high level of ionization efficiency. The gas flow rate L1 can be previously set so that the flow rate L1+L2 of the gas through the plasma generation area will be to some extent high so as to stabilize the plasma and ensure a high level of ionization efficiency.

The discharge ionization current detector of the present embodiment is characterized in that the cylindrical tube 2 having an outer diameter of 4 mm and an inner diameter of 2 mm (with a tube-wall thickness of 1 mm), which functions as the dielectric coating layer covering the surface of the plasma generation electrodes 4, 5 and 6, is made of quartz glass with a low OH content. Specifically, quartz glass with an OH content equal to or lower than 5 ppm (catalogue value) is used, which is comparatively easy to obtain as a high-accuracy infrared optical material. This design is aimed at minimizing the amount of hydrogen and oxygen released from the cylindrical tube 2 during the analysis.

An experiment for measuring the sensitivity, the baseline current value and other properties has been conducted with cylindrical tubes 2 made of various kinds of quartz glass and other dielectric materials. The result is hereinafter described. The dielectric materials used in the measurement are as follows:

(1) Normal quartz (with an OH content of 200 ppm or lower, produced by Momentive Performance Materials Inc., an American company)

(2) Low-OH-content quartz (with an OH content of 5 ppm or lower, produced by Momentive Performance Materials Inc.)

(3) A material prepared by performing a heat treatment on the normal quartz (with an OH content of 200 ppm) in a nitrogen-gas atmosphere at 1050° C. for eight hours.

(4) Sapphire (5) Alumina (Quality: TA010, produced by KYOCERA Corporation)

Figure 2A:
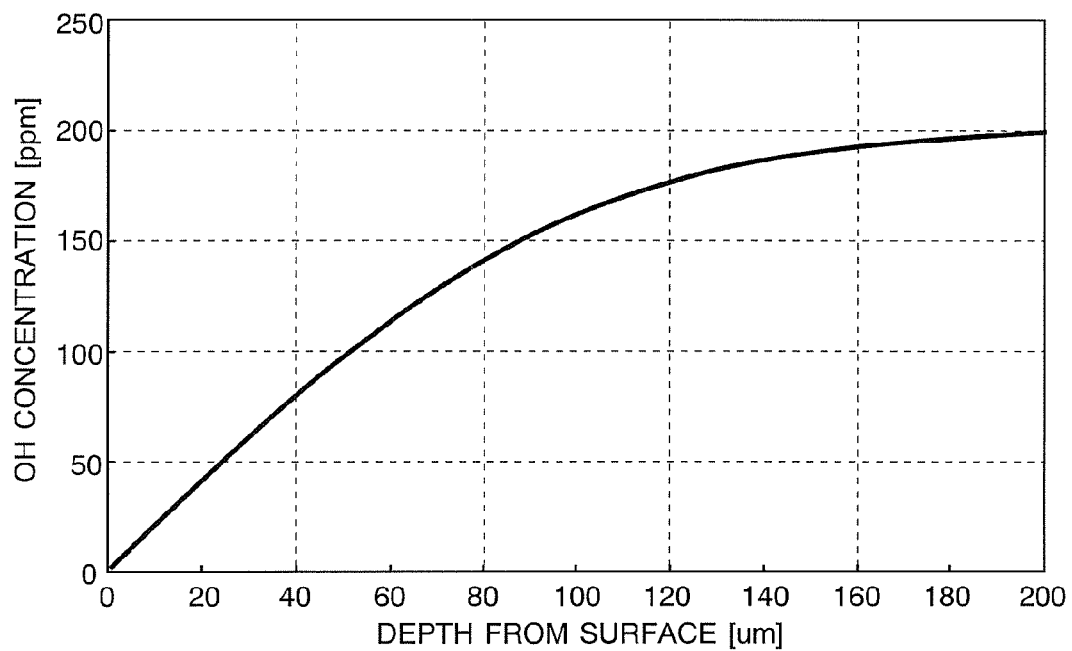
FIGS. 2A and 2B are graphs showing an OH-content distribution in the depth direction in the case where a glass material with an OH content of 200 ppm was heat-treated at 1000° C. for eight hours, where
Figure 2B:
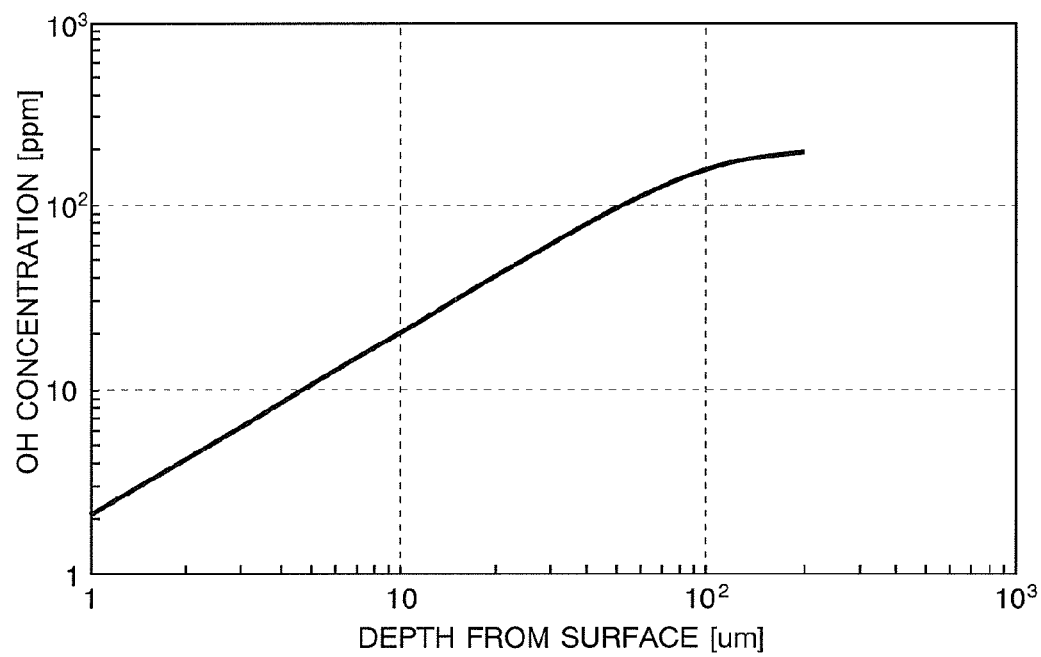

The temperatures used in the heat treatment of (3) are much higher than the normal annealing temperature (which is several hundred degrees Celsius at the highest level). According to a document (Nishimoto et al., "Evaluation of Silanol Concentration on Quartz Glass Surface for EOF Stability of CE Chip", *Micro Total Analysis Systems,* 2001, pp. 595-596), when quartz glass is heat-treated at such a high temperature as the aforementioned level, a region in which the OH content is significantly decreased is formed from the surface to a depth of several tens of micrometers. The OH-content distribution in the depth direction created by such a heat treatment can be calculated by means of a Fick's diffusion formula. When quartz glass having a total OH content of 200 ppm as in (3) is subjected to a heat treatment, the calculated OH-content distribution in the depth direction will be as shown in FIGS. 2A and 2B. The two figures show the same curve, where FIG. 2A is a graph with a linear scale and FIG. 2B is a graph with a logarithmic scale. FIGS. 2A and 2B demonstrate that the OH content is equal to or lower than 5 ppm within a region from the surface to a depth of approximately 2 μm, as in the case of quartz (2).

The sensitivity and the baseline current value were measured for five cylindrical tubes made of the five dielectric materials (1)-(5), respectively, using a standard sample (dodecane as the sample and hexane as the solvent). For (1)-(3), the detection limit was also calculated from the measured noise values. To cancel the variation in the sensitivity due to the difference in the material, structure and other factors, an equivalent flow rate of impurity was calculated by dividing the baseline current value by the sensitivity. The measurement result, accompanied by the result of the calculation based on the measurement result, is shown in Table 1.

TABLE 1

| Material | Sensitivity (nA · sec/ng) | Baseline Current (nA) | Equivalent Amount of Impurity (ng/sec) | Detection Limit (pgC/sec) |
|---|---|---|---|---|
| (1) Quartz (OH Content, 200 ppm) | 1.8 | 6.0 | 3.3 | 3-5 |
| (2) Quartz (OH Content, 5 pmp or lower) | 2.1 | 3.9 | 1.9 | 1.4 |
| (3) Quartz (OH Content, 200 ppm), heat-treated in N$_2$ at 1050° C. for 8 hours | 1.9 | 3.9 | 2.1 | 1.4 |
| (4) Sapphire | 2.7 | 5.6 | 2.1 | — |
| (5) Alumina | 1.7 | 2.9 | 1.7 | — |

As is clear from Table 1, it is possible to decrease the baseline current value and the equivalent flow rate of impurity by using any one of the dielectric materials (2)-(5) with low OH contents. Furthermore, the detection limit is improved with the decrease in the equivalent flow rate of impurity. The detection limit of the FIDs currently and widely used as detectors for GCs is approximately >1.5 pgC/sec. The result shows a detection limit better than that of the FID has been achieved by using (2) or (3).

Thus, with the discharge ionization current detector of the previously described embodiment using the cylindrical tube 2 made of quartz glass with a low OH content, it is possible to make the baseline current lower than that of the conventional discharge ionization current detectors, and thereby improves the detection limit to a level comparable to or even better than that of the FIDs. The dielectric materials (3)-(5) can also be used in place of the quartz glass with a low OH content.

In particular, the result obtained for (3) demonstrates that, for the 1-mm thickness of the wall of the cylindrical tube 2, the depth range with an OH content equal to or lower than 5 ppm is as small as 2 μm from the surface which comes in contact with the plasma. Accordingly, it can be expected that, even if the cylindrical tube is not entirely made of a dielectric material with a low OH content, the previously described effects, i.e. the low baseline current value and the adequately low detection limit due to the low baseline current, will similarly be obtained if at least the aforementioned depth range consists of a coating layer made of a low-OH-content material, such as (2), (4) or (5).

Figure 3:
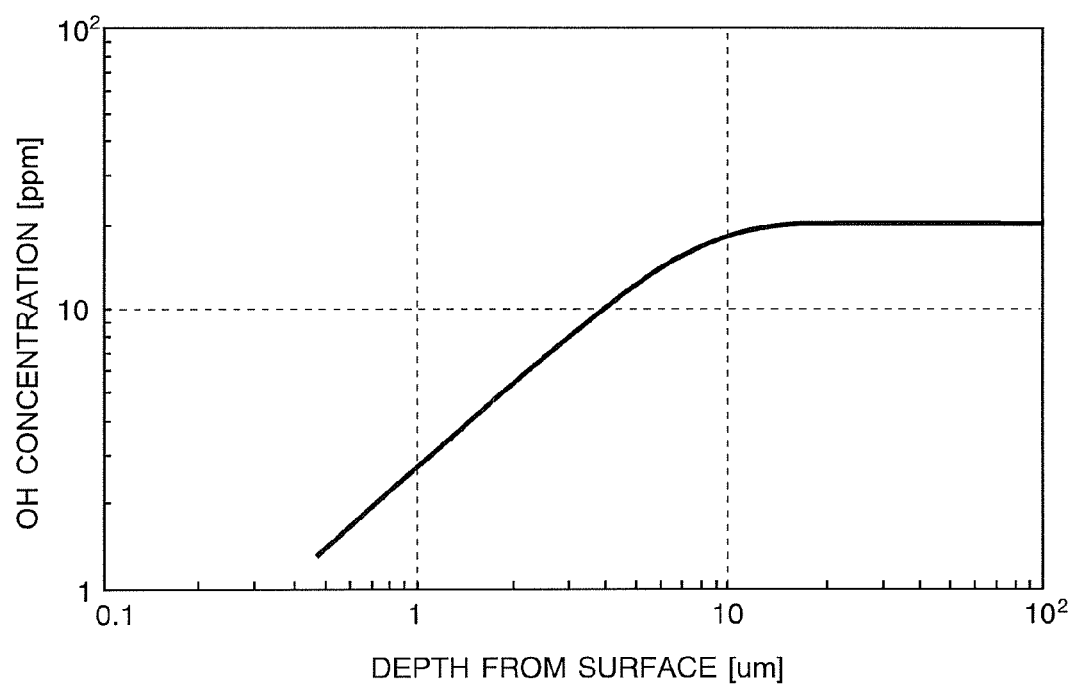
FIG. 3 is a graph showing an OH-content distribution in the depth direction in the case where a glass material with an OH content of 20 ppm was heat-treated at approximately 640° C. for five hours.

The heat treatment conditions in (3) can be changed according to the OH content of the bulk material. For example, when quartz glass having a total OH content of 20 ppm is subjected to a heat treatment at approximately 640° C. for five hours, the calculated OH-content distribution in the depth direction will be as shown in FIG. 3. This figure suggests that a region with an OH content equal to or lower than 5 ppm can be created from the surface to a depth of 2 μm, and high performances as shown in (3) can be expected. For a material with an OH content of 10 ppm, a heat treatment at 500° C. for 12 hours or longer will provide a similar result.

It can evidently be expected that similar effects will be obtained by covering the wall of the cylindrical tube with a low-OH-content material having a thickness of 2 μm or greater instead of creating a low-OH-content region by a heat treatment of the material of the tube wall. For example, a coating layer with a thickness of 2 μm or greater can be formed on the surface of the cylindrical tube 2 by sputtering, CVD or other deposition techniques using silica glass, silicon nitride, alumina, diamond-like carbon or other materials as the low-OH-content dielectric material.

If the inner wall of the cylindrical tube 2 becomes hot due to the generation of the plasma, and if an OH-content gradient exists in the depth direction as in the case of the material shown in (3), it is possible that the OH content in the vicinity of the surface increases with the increase in the operating time. However, since the low-frequency AC-excited dielectric barrier discharge barely generates heat, the temperature in the plasma generation area will not exceed 150° C. at any stages including the initial baking process which is performed when the system is set up. As a result, the OH diffusion coefficient is decreased to <1E-18 cm$^2$/sec, which is lower than ~1E-9 cm$^2$/sec for 1000° C. (or ~1E-13 cm$^2$/sec for 500° C.). This fact suggests that the distribution of the OH content in the depth direction which has been fixed by a heat treatment at 500° C. or higher temperatures will never change on a normal time scale, and the system can exhibit adequately stable performances for a long period of time.

It should be noted that the previously described embodiment is a mere example of the present invention, and any change, modification or addition appropriately made within the spirit of the present invention will naturally fall within the scope of claims of this patent application.

EXPLANATION OF NUMERALS

2 . . . Cylindrical Tube
3 . . . First Gas Passage
4, 5 and 6 . . . Plasma Generation Electrode
7 . . . Gas Supply Tube
8 . . . First Gas Discharge Tube
9 . . . First Flow-Rate Regulator
10 . . . Excitation High-Voltage Power Source
11 . . . Second Gas Passage
12 . . . Recoil Electrode
13 . . . Second Gas Discharge Tube
14 . . . Second Flow-Rate Regulator
15 . . . Insulating Member
16 . . . Bias Electrode
17 . . . Ion-Collecting Electrode
18 . . . Sample Introduction Tube
20 . . . Ion Current Detector
21 . . . Bias DC Power Source
22 . . . Current Amplifier

The invention claimed is:

1. A discharge ionization current detector, comprising: a discharge electrode having a surface covered with a dielectric member and provided so as to be exposed to an inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by an action of the plasma in the gas passage, wherein quartz glass with a hydroxyl-group content equal to or lower than 5 ppm is used as the dielectric member.

2. A discharge ionization current detector, comprising: a discharge electrode having a surface covered with a dielectric member and provided so as to be exposed to an inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by an action of the plasma in the gas passage, wherein a material prepared by performing a heat treatment on quartz glass with an upper limit of a hydroxyl-group content higher than 5 ppm at a temperature of 500° C. or higher in a predetermined kind of inert-gas atmosphere is used as the dielectric member.

3. A discharge ionization current detector, comprising: a discharge electrode having a surface covered with a dielectric member and provided so as to be exposed to an inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by an action of the plasma in the gas passage, wherein sapphire is used as the dielectric member, thereby reducing a concentration of impurities mainly composed of hydrogen and oxygen released from the discharge electrode into the plasma gas.

4. A discharge ionization current detector, comprising: a discharge electrode having a surface covered with a dielectric member and provided so as to be exposed to an inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by an action of the plasma in the gas passage, wherein high-purity alumina is used as the dielectric member, thereby reducing a concentration of impurities mainly composed of hydrogen and oxygen released from the discharge electrode into the plasma gas.

5. A discharge ionization current detector, comprising: a discharge electrode having a surface covered with a dielectric member and provided so as to be exposed to an inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by an action of the plasma in the gas passage, wherein the dielectric member has a thin-film layer made of a dielectric material with a hydroxyl-group content equal to or lower than 5 ppm and forming a 2-μm depth range from the surface coming in contact with plasma.

6. A discharge ionization current detector, comprising: a discharge electrode on a cylindrical tube covered with a dielectric member and provided so as to be exposed to an inside of a gas passage through which plasma gas is passed; an alternating voltage supplier for applying a low-frequency alternating voltage to the discharge electrode so as to generate a dielectric barrier discharge in the gas passage and thereby produce plasma from the plasma gas; and a current detector for detecting an ion current due to a sample component in a sample gas ionized by an action of the plasma in the gas passage, wherein a coating layer with a thickness of 2 μm or greater is formed on the surface of the cylindrical tube by deposition techniques using silica glass, silicon nitride, alumina, or diamond-like carbon as the low-OH-content dielectric material.

\* \* \* \* \*